(12) United States Patent  
Fowkes et al.

(10) Patent No.: US 7,536,644 B2
(45) Date of Patent: May 19, 2009

(54) METHOD AND SYSTEM FOR FACILITATING SELECTION OF STORED MEDICAL IMAGES

(75) Inventors: Kenneth M. Fowkes, Mountain View, CA (US); Laurence S. McCabe, Sunnyvale, CA (US); Paul D. Miller, Palo Alto, CA (US); David R. Mack, Saratoga, CA (US); Ruth E. Leibig, Palo Alto, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 686 days.

(21) Appl. No.: 10/184,729

(22) Filed: Jun. 27, 2002

(65) Prior Publication Data

US 2004/0001080 A1 Jan. 1, 2004

(51) Int. Cl.
*G06F 3/00* (2006.01)

(52) U.S. Cl. .................. 715/720; 715/817; 707/10; 600/407; 600/437; 600/440

(58) Field of Classification Search ............ 715/720, 715/817; 707/10, 817; 600/407
See application file for complete search history.

(56) References Cited

U.S. PATENT DOCUMENTS

| | | | | |
|---|---|---|---|---|
| 5,029,016 A | * | 7/1991 | Hiyama et al. | 358/403 |
| 5,124,789 A | * | 6/1992 | Hiyama et al. | 348/74 |
| 5,161,535 A | * | 11/1992 | Short et al. | 600/437 |
| 5,315,999 A | * | 5/1994 | Kinicki et al. | 600/443 |
| 5,452,416 A | * | 9/1995 | Hilton et al. | 715/783 |
| 5,715,823 A | * | 2/1998 | Wood et al. | 600/437 |
| 5,761,655 A | | 6/1998 | Hoffman | |
| 5,852,823 A | | 12/1998 | De Bonet | |
| 5,911,139 A | | 6/1999 | Jain et al. | |
| 5,920,317 A | * | 7/1999 | McDonald | 715/853 |
| 6,241,668 B1 | | 6/2001 | Herzog | |
| 6,253,214 B1 | * | 6/2001 | Hall et al. | 707/204 |

(Continued)

FOREIGN PATENT DOCUMENTS

JP 11353327 A 12/1999

(Continued)

OTHER PUBLICATIONS

DICOM standard, "Digital Imaging and Communications in Medicine (DICOM) Part 3: Information Object Definitions", Oct. 13, 2001, National Electrical Manufacturers Association, pp. 35, 36, 44-50, 204-213, 223-227, 250-260, Available http://web.archive.org/web/20011013150240/medical.nema.org/dicom/2000.html.*

(Continued)

*Primary Examiner*—Tadesse Hailu
*Assistant Examiner*—Alvin H Tan

(57) ABSTRACT

The preferred embodiments described herein provide a method and system for facilitating selection of stored medical images. In one preferred embodiment, a plurality of medical images are stored, and, for each medical image, the settings of at least one acquisition time control used to create the image are also stored. During image review, a user selects a set of acquisition time control settings, and a set of medical images is automatically selected from the stored images based on the selected set of acquisition time control settings. Other preferred embodiments are provided, and each of the preferred embodiments described herein can be used alone or in combination with one another.

21 Claims, 2 Drawing Sheets

U.S. PATENT DOCUMENTS

| | | | |
|---|---|---|---|
| 6,504,571 | B1 | 1/2003 | Narayanaswami et al. |
| 6,526,304 | B1* | 2/2003 | Patel et al. .................. 600/407 |
| 6,557,102 | B1* | 4/2003 | Wong et al. ................. 713/176 |
| 6,574,629 | B1* | 6/2003 | Cooke, Jr. et al. ............. 707/10 |
| 6,574,742 | B1* | 6/2003 | Jamroga et al. ............. 713/400 |
| 6,631,499 | B1 | 10/2003 | Tsujii |
| 6,728,424 | B1* | 4/2004 | Zhu et al. .................. 382/294 |
| 6,813,395 | B1 | 11/2004 | Kinjo |
| 6,954,767 | B1* | 10/2005 | Kanada ...................... 707/204 |
| 6,972,425 | B2 | 12/2005 | Tamakoshi et al. |
| 7,116,807 | B1 | 10/2006 | Brackett |
| 7,120,644 | B1* | 10/2006 | Canessa et al. ............. 707/102 |
| 7,171,612 | B2 | 1/2007 | Toda |
| 2001/0016056 | A1* | 8/2001 | Westphal et al. ............ 382/128 |
| 2001/0019587 | A1 | 9/2001 | Hashimoto et al. |
| 2001/0043729 | A1 | 11/2001 | Giger et al. |
| 2001/0052933 | A1* | 12/2001 | Nybo et al. .................. 348/207 |
| 2002/0016718 | A1 | 2/2002 | Rothschild et al. |
| 2002/0019832 | A1* | 2/2002 | Tanaka et al. ............... 707/500 |
| 2002/0023172 | A1* | 2/2002 | Gendron et al. ............. 709/238 |
| 2002/0059300 | A1* | 5/2002 | Nagata et al. ............ 707/104.1 |
| 2002/0071677 | A1 | 6/2002 | Sumanaweera |
| 2002/0169766 | A1 | 11/2002 | Aoyama |
| 2003/0005464 | A1 | 1/2003 | Gropper et al. |
| 2004/0001080 | A1 | 1/2004 | Fowkes et al. |
| 2004/0210586 | A1* | 10/2004 | Birdwell et al. ............. 707/100 |

FOREIGN PATENT DOCUMENTS

| | | |
|---|---|---|
| JP | H 11-353327 | 12/1999 |
| JP | 2000040117 A | 2/2000 |
| JP | 2001005825 A | 4/2000 |
| JP | 2000166878 A | 6/2000 |
| JP | 2000287940 A | 10/2000 |
| JP | 11-174232 | 1/2001 |
| JP | 2001-5825 | 1/2001 |
| JP | 2001155099 A | 6/2001 |

OTHER PUBLICATIONS

"Using Stress Echocardiography—HP SONOS 5500, HP SONOS 4500 User's Guide," Hewlett-Packard Company, pp. 1-6 to 1-9, 1-30 to 1-37, and 1-66 to 1-75 (Apr. 1999).

"Integration of Content-based Image Retrieval to Picture Archiving and Communication Systems," Lehmann et al., presented at MIE2003 (Medical Informatics in Europe 2003), http://libra.imib.rwth-aachen.de/irma/ps-pdf/MIE_2003-final.pdf (6 pages).

Nedevschi, S.; Olinic, D.; Gal, Z., et al; "Retrieval of DICOM Echocardiographic Images Using the Diagnosis and Biological Structure Features as Search Keywords," 2000, IEEE Computers in Cardiology; pp. 283-286, ISBN: 0-7803-6557-7.

Nedevschi, S.; Olinic, D.; Feier, C., et al; "A Structured Medical Text Field of DICOM 3.0 Transesophagal Echocardiography Image File for Database Implementation," 1999, IEEE Computers in Cardiology; pp. 443-446, ISBN: 0-7803-5614-4.

Nedevschi, S.; Olinic, D.; Gyongyi, Z.: "Feature Based Retrieval of Echocardiographic Images Using DICOM Structured Reporting," 2001, IEEE Computers in Cardiology; pp. 670-682, ISBN: 0-7803-7266-2.

* cited by examiner

METHOD AND SYSTEM FOR FACILITATING SELECTION OF STORED MEDICAL IMAGES

BACKGROUND

For many years, ultrasound images generated during an ultrasound exam were stored on VCR tape and retrieved using conventional VCR controls like fast forward. Because VCR tape provides only serial access to stored images, viewing a specific image in a recorded exam requires a user to scan through all of the prior images in the series, which is a slow and manual process. VCR storage has largely been replaced with digital storage to random access media, such as memory or disk. However, digital storage of ultrasound images is not as fully utilized in existing ultrasound systems as it could be because exams are still presented to users as a serial collection of images, which a user must manually scan through to select a specific image. Selecting an image in this manner is time consuming because:

(1) Images are large files that take a relatively long time to load from storage media;
(2) Images are often compressed, and time is required to decompress the images;
(3) Visual examination of each image takes time; and
(4) The operation of advancing to the next image in a series requires an action by the user.

Several methods can be used to facilitate the selection of a stored medical image, but each has its own disadvantages. For example, image load time can be improved by adopting faster hardware, but this increases system cost. Also, the time required to advance to a next image in a series can be reduced by displaying multiple images of smaller size; however, the smaller image size can interfere with a sonographer's ability to examine each image.

There is a need, therefore, for an improved method and system for facilitating selection of stored medical images.

SUMMARY

The present invention is defined by the following claims, and nothing in this section should be taken as a limitation on those claims.

By way of introduction, the preferred embodiments described below provide a method and system for facilitating selection of stored medical images. In one preferred embodiment, a plurality of medical images are stored, and, for each medical image, the settings of at least one acquisition time control used to create the image are also stored. During image review, a user selects a set of acquisition time control settings, and a set of medical images is automatically selected from the stored images based on the selected set of acquisition time control settings. Other preferred embodiments are provided, and each of the preferred embodiments described herein can be used alone or in combination with one another.

The preferred embodiments will now be described with reference to the attached drawings.

DETAILED DESCRIPTION OF THE PRESENTLY PREFERRED EMBODIMENTS

Figure 1:
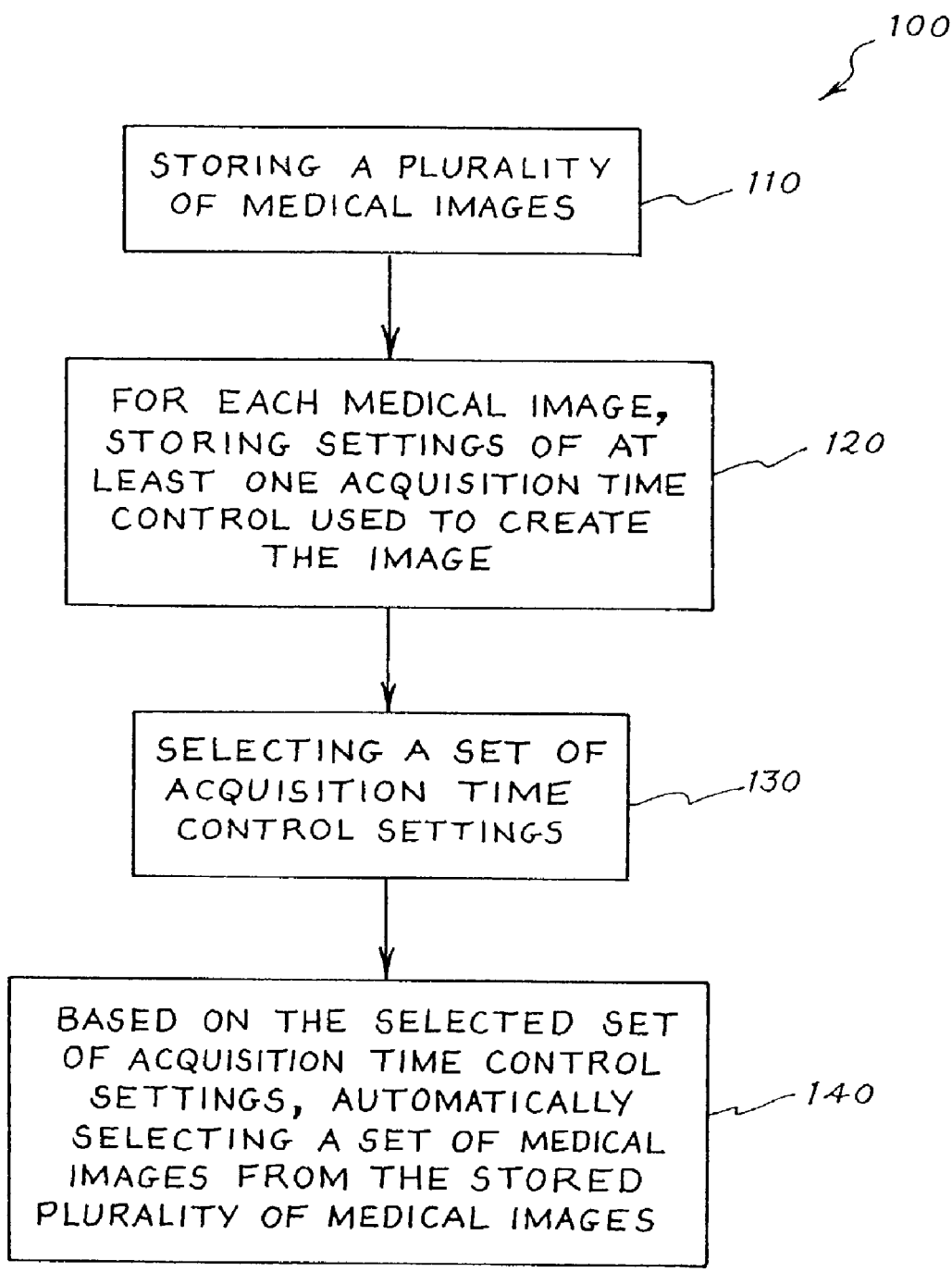
FIG. 1 is a flow chart of a method of a preferred embodiment for facilitating selection of stored medical images.

By way of overview, the preferred embodiments described below relate to a method and system for facilitating selection of stored medical images. With these preferred embodiments, a user can more quickly retrieve a desired medical image from a collection of stored images by manipulating the same controls that were used to acquire the desired image in the first place. With reference to the flow chart 100 of FIG. 1, in one preferred embodiment, medical images generated by a medical image acquisition device are stored in one or more storage devices (act 110). For each of the stored images, the settings of at least one acquisition time control used to create the image are also stored (act 120). To select a stored image, a user selects a set of acquisition time control settings (act 130), and based on the selected settings, a set of medical images is automatically selected from the stored images (act 140).

Figure 2:
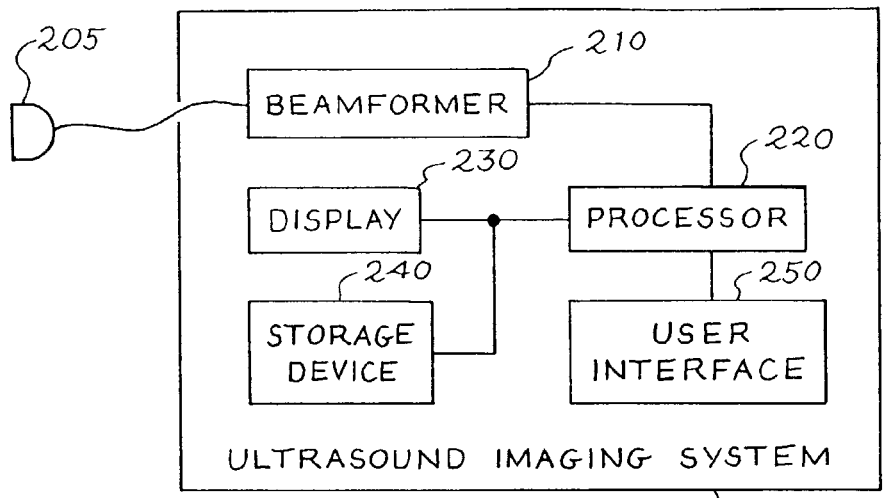
FIG. 2 is a block diagram of a medical diagnostic ultrasound imaging system of a preferred embodiment.

Turning again to the drawings, FIG. 2 is a block diagram of a medical diagnostic ultrasound imaging system 200 that will be used to illustrate the operation of the method shown in FIG. 1. While an ultrasound system and ultrasound images are used in this illustration, it should be noted that other types of medical image acquisition devices and medical images can be used with these preferred embodiments. As shown in FIG. 2, the ultrasound system 200 comprises a transducer probe 205, a beamformer 210, a processor 220, a display device 230, a storage device 240, and a user interface 250. The term "processor" broadly refers to the appropriate hardware and/or software components of the ultrasound system 200 that can be used to implement the functionality described herein. The storage device 240 is suitable for storing digital images and can take the form, for example, of a solid-state volatile or non-volatile memory device or a permanent or removable optical or magnetic disk. The user interface 250 can include, for example, physical knobs, buttons, or keys that a user can physically manipulate on a control panel; soft buttons displayed on the display device 230 that a user can select with a pointing device or by touching the displayed button if the display device 230 is touch-sensitive; or a microphone through which a user can voice commands. The ultrasound system 200 can comprise additional components, which are not shown in FIG. 2 for simplicity. For example, the ultrasound system 200 can comprise an additional memory device (computer-usable media) that stores software (computer-readable program code) run by the processor 220.

In operation, a sonographer uses the user interface 250 to select a set of acquisition time controls settings. As used herein, the term "set" refers to a group of one or more, and the term "acquisition time control" refers to any control that a user manipulates in the process of acquiring a medical image to affect how the medical image is acquired. Manipulating an acquisition time control can affect transmit, receive, and/or processing operations. For a medical diagnostic ultrasound imaging system, an acquisition time control can be a "major mode" key that a user selects to choose the type of ultrasound image that will be generated (e.g., M-mode, B-mode, color flow, or Spectral Doppler (PW)). An acquisition time control can also be a flow sub-mode with Doppler Tissue Imaging or contrast imaging settings. Additionally, an acquisition time control can be an individual parameters (e.g., frequency or depth) or a "pre-set," which is a stored combination of individual acquisition time control settings (e.g., specific mode, frequency, and depth settings) grouped together based on the anatomy being imaged (e.g., general radiology, vascular examination, cardiology) or the sonographer performing the examination (e.g., Dr. Smith, Dr. Robert).

During an ultrasound examination, the sonographer contacts the transducer probe 205 with a patient, and the ultrasound system 200 acquires an ultrasound image in accordance with the acquisition time control settings. In general, the ultrasound system's processor 220 causes the beamformer 210 to apply a voltage to the transducer 205 to cause it to vibrate and emit an ultrasonic beam into the portion of the patient's body in contact with the transducer 205. Ultrasonic energy reflected from the patient's body impinges on the transducer 205, and the resulting voltages created by the transducer 205 are received by the beamformer 210. The processor 220 processes the sensed voltages to create an ultrasound image and displays the image on the display device 230. In addition to being displayed on the display device 230, a generated ultrasound image can also be stored in digital form. For example, the sonographer can be given the option of storing an ultrasound image by pressing an "image capture" key on the user interface 250, or, alternatively, the ultrasound image can be automatically stored without user intervention. In this way, a series of images from an ultrasound exam can be stored in the storage device 240 in the ultrasound system 200 for later review. While shown as a single box in FIG. 2, the storage device 240 can comprise one or more individual storage devices (e.g., two separate disks). Additionally, as will be described below, an ultrasound image can be stored in a storage device external to the ultrasound system 200.

In this preferred embodiment, for each stored ultrasound image, some or all of the acquisition time control settings used to create the image are also stored. As will be described below, the stored acquisition time control settings can later be used as a selection criteria for selecting a stored image. The acquisition time control settings for an image can be stored in any suitable manner and can be stored before, during, or after the storage of its associated image. The settings can be stored along with the image, such as when the settings are stored in a Digital Imaging and Communications in Medicine (DICOM) tag attached to an image. Alternatively, a separate file comprising the acquisition time control settings can be stored for each stored image. The separate file can be stored in the same storage device that stores the image or in a different storage device. Preferably, a directory is used for a collection of stored images (e.g., images from a given exam) to store the acquisition time control settings for each image in the collection. The directory can be stored in the storage device that stores the images or can be stored in a separate location. Storing acquisition time control settings for multiple images in a directory allows review software to more quickly identify an image since searching a single directory for the search criteria is faster than searching each stored image or file individually.

In prior ultrasound systems, to retrieve an image from a stored exam, a user selects an "image review mode" using the user interface, and the processor retrieves all of the images in the exam. To find an image of interest, the user manually views each of the images. Consider, for example, the situation in which a sonographer captures 50 images of a patient during an exam, 45 of which are B-mode images and five of which are Spectral Doppler images. If the sonographer were interested in reviewing the Spectral Doppler images, he would scan though the series of 50 images until he found the five Spectral Doppler images. As discussed in the background section, this retrieval process can be time consuming and tedious for the sonographer.

To facilitate the selection of a stored image, the ultrasound system 200 in this preferred embodiment allows a user to filter the stored images using the acquisition time control settings stored with the images. In operation, after the user enters the image review mode, he manipulates the acquisition time controls of the user interface 250 to select a set of acquisition time control settings. The number of settings selected as search criteria can be the same as, more than, or less than the number of setting used to generate the image of interest. Based on these settings, a set of the stored medical images is automatically selected from the group of stored images. With reference to the previous example in which a sonographer is interested in reviewing Spectral Doppler images, during image review mode, the sonographer would press the Spectral Doppler button. The review software would search the acquisition time control settings stored for the stored images and automatically select the five Spectral Doppler images from the 50 stored images, thereby filtering out all images that were not associated with the Spectral Doppler setting. By using these preferred embodiments to narrow the search to a subset of the stored images, the number of images that a user needs to load and visually examine is reduced, thereby allowing the user to more quickly find a desired image.

The results of the automatic selection can be presented to the user in any suitable manner. For example, the processor 220 can present a list of the automatically selected images to the user, and the user can select an image for viewing from this list. Instead of presenting a list, the review software can automatically retrieve and display the selected set of images (e.g., in a thumbnail format). Additionally, the functionality of "next image" and "previous image" operations can be adjusted to skip over images that do not match the specified acquisition time control settings.

Regardless of how the images are presented, the images can be sorted in order of their closeness to the specified acquisition time control settings. For example, in an ultrasound system utilizing position sensing, moving a Doppler Gate to a specific location in one image can order the images in the exam so that those with Doppler spectra collected from close to the specified Gate location would be in front of images with Doppler spectra collected far from the current Gate location. Images can also be sorted based on other criteria. For example, clicking on a particular image can initialize a search/sort criteria to order images by their closeness to the selected image. Criteria can then be manually turned off in order to widen the search. As another example, the review software can analyze the selected set of images to determine the similarities/differences between the images and then provide the user with an indication of those similarities/differences to help the user narrow the search. For example, consider the situation in which the review software automatically selects a set of ten images, five of which were acquired at one frequency and five of which were acquired at another frequency. The review software can automatically illuminate the frequency key to inform the user that he can narrow the images even further by pressing the button and selecting a specific frequency.

There are several alternatives that can be used with these preferred embodiments. In the preceding examples, an exact match selection scheme was used in which only those images whose stored settings exactly matched the selected set of acquisition time control settings were automatically selected. Other selection schemes can be used. For example, a selection scheme can be used where those images whose stored settings most closely match (instead of exactly match) the selected set of acquisition time control settings are automatically selected. Consider, for example, the situation in which a sonographer is looking for a long-axis, Color Doppler view of the heart. During image review, the sonographer selects the Long-Axis Preset and presses the Color Doppler mode key. If none of the stored images are stored with both the Long-Axis and Color Doppler settings, the review software can present the closest match (e.g., images stored with either the Long-Axis setting or the Color Doppler setting). Further, relational selection schemes, such as greater than, greater than or equal to, less than, less than or equal to, or not equal to, can also be used. For example, some acquisition time controls (such as depth) can be incremented or decremented, and the direction of the change applied by a user can be used to establish the relational selection criteria (e.g., increasing the depth control filters out images with depths that are shallower than the current depth setting, while decreasing the depth control filters out images with depths deeper than the current depth setting).

As noted above, the automatic selection of images is "based on" the selected set of acquisition time control settings. Any selection that at least in part uses the selected set of acquisition time control settings is "based on" that selected set. While the acquisition time control settings can be the sole search criteria, other information related to and stored along with an image can be used along with the acquisition time control settings. Such additional information includes, but is not limited to, identification of the probe used to generate an image, the location of the probe (indicated by a position sensing device), the presence or absence of a biopsy needle in the image, annotations, and stage timer values. Additionally, it should be noted that while the stored images that were searched in the examples described above were of the same patient and generated in the same exam, the stored images that are searched can be generated over multiple exams and be of different patients. This would allow a user to easily access images acquired for different patients and/or during different exams, but related to the same anatomy, for comparison purposes.

In the embodiments described above, the selection of acquisition time controls during image review was made using the user interface 250 of the ultrasound system 200. There are several advantages to using the user interface 250 of the ultrasound system 200 to enter search criteria: (1) acquisition time controls are very familiar to sonographers, (2) the user interface 250 of the ultrasound system 200 is designed so that the acquisition time controls are fast and easy to use; and (3) many acquisition time controls have strong associations with image content, so manipulating them feels like a natural way for sonographers to find images with specific content. All of these advantages contribute to making this technique of facilitating selection of a stored image easy for sonographers to adopt with a very short learning curve.

Figure 3:
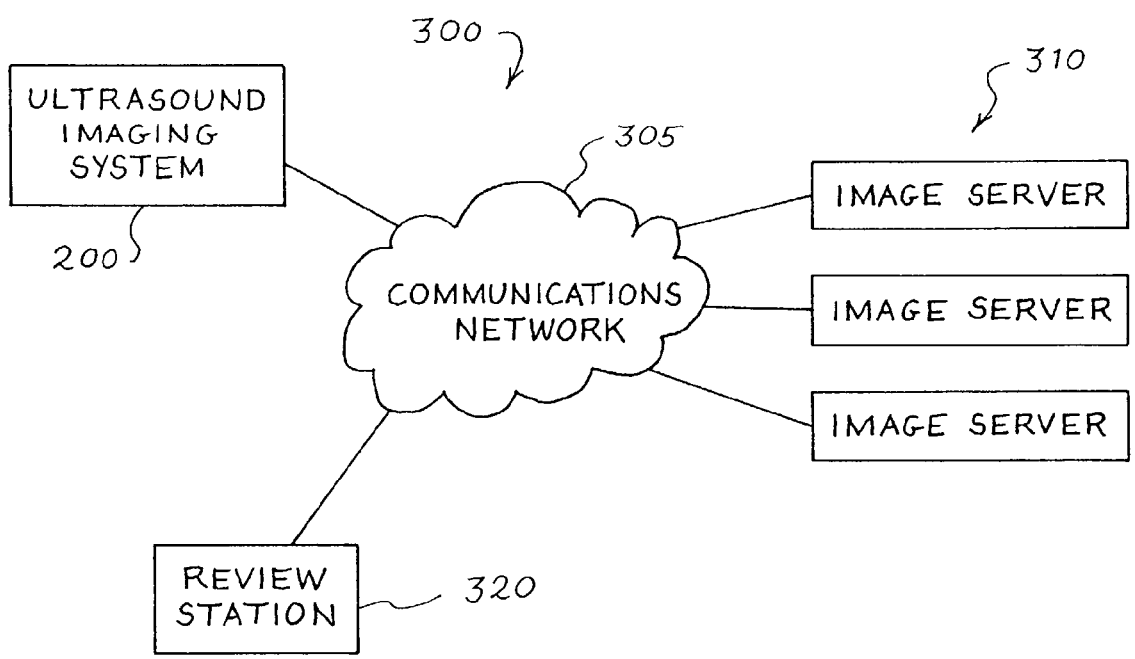
FIG. 3 is a block diagram of a network environment of a preferred embodiment.

In another preferred embodiment, instead of using a user interface of an ultrasound system, an image review station is used to select acquisition time control settings for image retrieval. This preferred embodiment will be illustrated in conjunction with FIG. 3. FIG. 3 is an illustration of a network environment 300 comprising an ultrasound system 200, one or more image servers 310, and a review station 320, all connected to a communications network 305 (e.g., the Internet, a hospital or clinic intranet, etc.). In this environment 300, images generated by the ultrasound system 200 can be stored either in the storage device 240 of the ultrasound system or in the image servers 310. The review station 320 is a computer workstation comprising a processor, a display device, and a user interface. The review station 320 comprises image review software that allows a user to retrieve a stored image and perform measurements and other actions on that image. In this embodiment, the image review software also comprises the functionality to input acquisition time control settings and to automatically select images based on those settings. For example, the review software can display a control panel with soft buttons mimicking the look of a control panel of an ultrasound system. After the user selects the acquisition time control settings using this "virtual control panel," the review software on the review station 320 can search the stored images for the selected settings. Alternatively, a user can use the review station 320 to type or otherwise enter the acquisition time control settings into a search engine.

It should be noted that each of the acts in the method shown in FIG. 1 can be performed by executing computer-readable program code stored on computer-usable media (e.g., one or more memories or disk drives). Further, the computer-readable program code can be located in any suitable location in the network environment 300. For example, the computer-readable program code implementing the functionality of automatically selecting a set of medical images based on acquisition time control settings can be stored in computer-usable media in the ultrasound system 200, review station 320, image server 310, or other components (not shown) of the network environment 300.

With the preferred embodiment described above, a desired item is retrieved from a stored collection of items by manipulating the same controls that would be used to generate the item. These preferred embodiments can be applied to a variety of applications, such as to ultrasound systems with very high acquisition rates. Advances in ultrasound technology have the potential to produce acquisition rates that far exceed the ability of display systems (or sonographers) to process. For example, one might imagine acquiring a data set that could be reconstructed to produce a strip-type display (M-mode or Doppler) from any point in the field of view. Since this amount of information cannot be viewed in real-time, such a data set would have to be reviewed after the fact. A very natural way for the sonographer to specify the location of interest for after-the-fact reconstruction would be to move a Cursor or Gate control to that location. The concept of using acquisition time controls for quick access to acquired data during review at a later time is also useful outside of medical imaging context. Consider, for example, a set-top box (e.g., TiVo) that records many shows from many channels. Currently, one selects a particular show by scrolling through a list of recorded programs. Applying these preferred embodiments to this scenario, a user would select a channel and/or recording time using the standard buttons on his remote (the acquisition time control) to get a shorter list that contains only programs recorded from that channel and/or at the specified time.

Finally, as noted above, although ultrasound images were used to illustrate the preferred embodiments, any type of medical image can be used. Medical images include still or moving images ("clips") generated from any imaging modality including, but not limited to, ultrasound, computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy. The following claims should not be limited to a specific type of medial image unless explicitly recited therein.

It is intended that the foregoing detailed description be understood as an illustration of selected forms that the invention can take and not as a definition of the invention. It is only the following claims, including all equivalents, that are intended to define the scope of this invention.

What is claimed is:

1. A method for facilitating selection of stored medical images, the method comprising:
    (a) storing a plurality of medical images, wherein the plurality of medical images are acquired by a medical image acquisition device;
    (b) for each medical image, storing settings of at least one acquisition time control of the medical image acquisition device used to acquire the image, wherein an acquisition time control of the medical image acquisition device comprises a control that is manipulated in a process of acquiring the image to affect how the image is acquired, wherein manipulating the acquisition time control affects one or more of transmit, receive, and processing operations;
    (c) receiving a set of acquisition time control settings used to acquire at least one medical image that a user wants to retrieve from the stored plurality of medical images, wherein the set of acquisition time control settings are selected by the user by manipulating the same at least one acquisition time control of the medical image acquisition device that was manipulated in the process of acquiring the at least one medical image, and wherein the received set of acquisition time control settings are at least some of the same settings used to acquire the at least one medical image; and
    (d) based on the set of acquisition time control settings received in (c), automatically selecting a set of medical images from the stored plurality of medical images.

2. The method of claim 1, wherein (a) comprises storing the plurality of medical images in the medical image acquisition device.

3. The method of claim 1, wherein (a) comprises storing the plurality of medical images in a server in communication with the medical image acquisition device.

4. The method of claim 1, wherein (b) comprises storing the settings in a tag along with the image.

5. The method of claim 1, wherein (b) comprises storing the settings in a file separate from the image.

6. The method of claim 1, wherein (b) comprises storing the settings in a directory.

7. The method of claim 1, wherein (d) comprises comparing the settings stored in (b) with the set of acquisition time control settings received in (c).

8. The method of claim 1, wherein (d) comprises automatically selecting a set of medical images whose stored settings exactly match the set of acquisition time control settings received in (c).

9. The method of claim 1, wherein (d) comprises automatically selecting a set of medical images whose stored settings most closely match the set of acquisition time control settings received in (c).

10. The method of claim 1 wherein (d) comprises automatically selecting a set of medical images using relational selection criteria.

11. The method of claim 1 further comprising: (e) providing a list of the set of medical images automatically selected in (d).

12. The method of claim 1 further comprising: (e) displaying the set of medical images automatically selected in (d).

13. The method of claim 1 further comprising: (e) in response to one of a next or previous image command, displaying an image from the set of medical images automatically selected in (d).

14. The method of claim 1 further comprising: (e) sorting the set of medical images automatically selected in (d).

15. The method of claim 1, wherein the plurality of medical images comprises ultrasound images.

16. A medical image acquisition device comprising:
    a user interface comprising a plurality of acquisition time controls, wherein an acquisition time control comprises a control that is manipulated in a process of acquiring a medical image to affect how the image is acquired, wherein manipulating at least one acquisition time control affects one or more of transmit, receive, and processing operations of the medical image acquisition device;
    at least one storage device storing a plurality of medical images and, for each medical image, settings of at least one acquisition time control of the medical image acquisition device used to acquire the image; and
    computer-usable media storing computer-readable program code for automatically selecting a set of medical images from the stored plurality of medical images based on a set of acquisition time control settings used to acquire at least one medical image that a user wants to retrieve from the stored plurality of medical images, wherein the set of acquisition time control settings are selected by the user by manipulating the same at least one acquisition time control of the user interface that was manipulated in the process of acquiring the at least one medical image, and wherein the selected set of acquisition time control settings are at least some of the same settings used to acquire the at least one medical image.

17. The medical image acquisition device of claim 16, wherein the plurality of medical images comprises ultrasound images.

18. The medical image acquisition device of claim 16, wherein the computer-usable media further stores computer-readable program code for providing a list of the automatically selected set of medical images.

19. The medical image acquisition device of claim 16, wherein the computer-usable media further stores computer-readable program code for displaying the automatically selected set of medical images.

20. The medical image acquisition device of claim 16, wherein the computer-usable media further stores computer-readable program code for displaying an image from the automatically selected set of medical images in response to one of a next or previous image command.

21. The medical image acquisition device of claim 16, wherein the computer-usable media further stores computer-readable program code for sorting the automatically selected set of medical images.

* * * * *